US010317327B2

(12) United States Patent
Corbett

(10) Patent No.: US 10,317,327 B2
(45) Date of Patent: Jun. 11, 2019

(54) PARTICLE CHARACTERIZATION

(71) Applicant: Malvern Panalytical Limited, Malvern, Worcestershire (GB)

(72) Inventor: Jason Cecil William Corbett, Malvern (GB)

(73) Assignee: Malvern Panalytical Limited, Malvern, Worcestershire (GB)

( * ) Notice: Subject to any disclaimer, the term of this patent is extended or adjusted under 35 U.S.C. 154(b) by 0 days.

(21) Appl. No.: 15/507,155

(22) PCT Filed: Sep. 7, 2015

(86) PCT No.: PCT/GB2015/052574
§ 371 (c)(1),
(2) Date: Feb. 27, 2017

(87) PCT Pub. No.: WO2016/034902
PCT Pub. Date: Mar. 10, 2016

(65) Prior Publication Data
US 2017/0276585 A1    Sep. 28, 2017

(30) Foreign Application Priority Data

Sep. 5, 2014 (GB) .................................. 1415783.8

(51) Int. Cl.
*G01N 15/02* (2006.01)
*G01N 21/47* (2006.01)
(Continued)

(52) U.S. Cl.
CPC ....... *G01N 15/0205* (2013.01); *G01N 21/474* (2013.01); *G01N 21/51* (2013.01);
(Continued)

(58) Field of Classification Search
CPC .. G01N 15/0205; G01N 15/042; G01N 21/51; G02B 6/32; G01J 3/4412; G01J 3/0218
See application file for complete search history.

(56) References Cited

U.S. PATENT DOCUMENTS 3,504,183 A    3/1970  Salkowski et al.
4,715,708 A *  12/1987 Ito ..................... G01N 15/1434
                                                      250/201.4
(Continued)

OTHER PUBLICATIONS

International Search Report and Written Opinion dated Nov. 20, 2015, directed to International Application No. PCT/GB2015/052574; 11 pages.

*Primary Examiner* — Sang H Nguyen
(74) *Attorney, Agent, or Firm* — Morrison & Foerster LLP

(57) ABSTRACT

A particle characterization apparatus is disclosed comprising: a sample cell for holding a sample, a light source for producing a light beam for illuminating the sample in the sample cell, thereby producing scattered light by the interaction of the light beam with the sample; a focussing lens for focussing the light beam within the sample; and a detector for detecting the backscattered light along a detection optical path that intersects the focussed light beam within the sample. The intersection of the light beam and the detection optical path in the sample define a detection region. The apparatus comprises an optical arrangement for varying the volume of the detection region.

17 Claims, 4 Drawing Sheets

(51) Int. Cl.
*G02B 6/32* (2006.01)
*G01N 21/51* (2006.01)
*G01N 15/00* (2006.01)

(52) U.S. Cl.
CPC ........... *G02B 6/32* (2013.01); *G01N 2015/03* (2013.01); *G01N 2021/4709* (2013.01); *G01N 2021/4728* (2013.01)

(56) References Cited

U.S. PATENT DOCUMENTS

| | | | |
|---|---|---|---|
| 4,896,961 A | | 1/1990 | Ito |
| 5,847,400 A | * | 12/1998 | Kain ................... G01N 21/6428 250/458.1 |
| 2007/0252984 A1 | * | 11/2007 | Van Beek ................. G01J 3/02 356/311 |
| 2010/0158508 A1 | * | 6/2010 | Kim ..................... H04N 5/2253 396/529 |
| 2011/0108531 A1 | * | 5/2011 | Stokes ................. B23K 26/364 219/121.69 |
| 2014/0132943 A1 | * | 5/2014 | Chou ..................... G01N 21/49 356/28.5 |
| 2014/0226158 A1 | * | 8/2014 | Trainer ................... G02B 6/32 356/336 |
| 2016/0202164 A1 | * | 7/2016 | Trainer ............. G01N 15/0211 356/336 |

* cited by examiner

PARTICLE CHARACTERIZATION

CROSS-REFERENCE TO RELATED APPLICATIONS

This application is a national phase filing under 35 USC § 371 of International Application No. PCT/GB2015/052574, filed on Sep. 7, 2015, and which claims priority to Great Britain Patent Application 1415783.8, filed on Sep. 5, 2014, the contents of which prior applications are incorporated herein by reference.

FIELD OF THE INVENTION

The present invention relates to a method and apparatus for particle characterization.

BACKGROUND OF THE INVENTION

Photon correlation spectroscopy (or dynamic light scattering, DLS) measures the time resolved signal scattered from particle suspensions. The relaxation time of the sample is determined from the correlation function of the scattered signal from which the particle size distribution can be estimated. The technique works best when each particle in suspension scatters light from the illuminating light beam (e.g. laser) only and not light that has already been scattered from other particles. At high concentrations multiple scattering tends to degrade the technique.

Within a small range of backscattered angles, multiply scattered signals may have an almost identical relaxation time (from which the particle size is calculated) to the singly scattered signal.

An existing technique (which may be termed non-invasive back scatter, or NIBS) uses a moving lens to place an illuminating laser optical path and a backscatter detection optical path into a variable position within a sample cuvette, as shown in FIGS. 1 and 2. The intersection of the illuminating optical path and the detection optical path may be termed the detection region.

When the sample is turbid (i.e. has a high concentration of particles), the detection region can be placed near to the cell wall, which significantly reduces multiple scattering due to the foreshortened illumination path length within the sample. In addition, a backscatter angle may be selected at which multiply scattered signals have a similar relaxation time to singly scattered signals, as already described.

Moving the detection region within the cell is advantageous, and it is also advantageous to maintain a selected angle of detection throughout the range of movement, so as to combine both benefits mentioned above.

At low particle concentration, the detection region may be moved toward the cell centre, or at least away from the static scattering contribution from the wall. Whilst the static scattering contribution from the wall may be negligible compared with the scattering contribution from particles in a high concentration sample, such static scattering from the wall may be a source of uncorrelated noise (or even static reference signal), for low concentration samples. The static scattering contribution from the wall may therefore decrease signal to noise ratio. The static scattering increases the correlogram baseline and thence reduces its intercept, which is a measure of the signal-to-noise of the measurement. Moving the detection region away from the cell wall may therefore improve the signal to noise ratio.

In the low sample concentration limit, DLS suffers from number fluctuations, whereby the scattered signal varies because of the fluctuation in the number of particles within the detection region, in addition to the contribution to the scattering from the Brownian motion of the particles. However, it may not be practical to simply expand the size of the detection beam to accommodate more particles, because this may increase the size of the beam out of a single coherence area. The highest signal-to-noise measurements using DLS may rely on measurement from within a single coherence area.

The signal to noise ratio of the correlogram is generally interpreted from the intercept of the correlogram and the y-axis. In order to maximize this value a single mode fibre may be used in the detection optical path, to select out a single spatial frequency from the 'image' of the speckle field. Simply increasing the size of the detection optical path may result in non-optimal coupling into such a fibre or may collect light from more than one coherence area, which may reduce the signal to noise ratio.

A method and apparatus for solving or ameliorating at least some of the above mentioned problems is desirable.

SUMMARY OF THE INVENTION

According to a first aspect of the invention, there is provided a particle characterization apparatus comprising: a sample cell for holding a sample, a light source for producing a light beam for illuminating the sample in the sample cell, thereby producing scattered light (e.g. backscattered light) by the interaction of the light beam with the sample; a focussing lens for focussing the light beam within the sample; and a detector for detecting the scattered light along a detection optical path that intersects the focussed light beam within the sample, the intersection of the focussed light beam and the detection optical path in the sample defining a detection region; wherein the apparatus comprises an optical arrangement for varying the volume of the detection region.

The apparatus may be configured to allow the position of the detection region within the sample to be varied. For turbid samples the detection region may be located near a sample cell wall and a small detection region used (by adjusting the beam width incident on the focussing lens to be relatively large). For samples with a low particle concentration, the detection region may be located remote from the sample cell wall, and a relatively large detection region used.

In some embodiments, the ability to adjust the volume of the detection region allows the measurement parameters of the particle characterization process to be better optimised to the properties of the sample, thereby improving signal to noise ratio for samples with high and/or low particle concentrations. Adjustment of both the location and volume of the detection region facilitates improved optimization of the measurement parameters, and enables significant improvements in the lowest and/or highest concentration of particles that can reliably be characterized.

The optical arrangement for varying the volume of the detection region may be operable to vary the light beam width incident on the focussing lens.

The optical arrangement for varying the light beam width incident on the focussing lens may comprise a beam expander.

The beam expander may comprise a moveable lens, operable to vary the light beam width incident on the focussing lens with movement of the moveable lens.

The beam expander may further comprise a fixed lens between the light source and the moveable lens.

The beam expander may be operable to produce a collimated output beam of variable width (e.g. from a collimated input beam, although this is not essential).

The fixed lens may comprise a diverging lens or a converging lens.

The moveable lens may comprise a converging lens.

The focussing lens may focus the detection optical path within the sample.

The focussing lens may be moveable, so as to vary a location of a focal plane of the light beam in the sample with movement of the focussing lens.

Moving the focussing lens may also vary the location of a focal plane of the detection optical path, thereby varying the position of the detection region within the sample with movement of the focussing lens.

The optical arrangement for varying the light beam width incident on the focussing lens may comprise: a converging lens between the focussing lens and light source causing the light beam to be convergent at the focussing lens, and an actuator operable to move the focussing lens so as to vary the distance between the focussing lens and the converging lens.

The converging lens (of the optical arrangement) may be a fixed lens.

The detection optical path may comprise an optical fibre.

The optical fibre may comprise a single mode fibre.

The apparatus may further comprise a coupling lens arranged to couple the detection optical path to the optical fibre.

The coupling lens may comprise a graded refractive index lens.

The focussing lens may comprise a focus tuneable lens.

The apparatus may be operable to perform a dynamic light scattering measurement using an output from the detector.

The apparatus may comprise a processor for performing the dynamic light scattering measurement.

According to a second aspect, there is provided a method of performing a dynamic light scattering measurement, comprising:
  adjusting a location and a volume of a detection region in a sample cell in response to a concentration of particles within a sample held by the sample cell;
  illuminating the sample with a light beam, thereby producing scattered light by the interaction of the light beam with the sample;
  detecting scattered light along a detection optical path that intersects the light beam within the sample at the detection region;
  deriving characteristics of particles within the sample from the detected scattered light by performing a dynamic light scattering analysis.

Adjusting the location and volume of the detection region may comprise moving the detection region closer to a wall of the sample cell through which the illumination light beam passes to illuminate the sample and reducing the volume of the detection region.

The adjusting may be in response to a concentration of particles that is greater than a first predetermined threshold.

Adjusting the location and volume of the detection region may comprise moving the detection region further from a wall of the sample cell through which the illumination light beam passes to illuminate the sample, and increasing the volume of the detection region.

The adjusting may be in response to a concentration of particles that is lower than a second predetermined threshold.

The method may further comprise providing an estimated concentration of particles within the sample cell.

The estimated concentration may comprise a qualitative indicator of concentration.

The method may further comprise measuring the concentration of particles within the sample.

Features of the first aspect may be combined with features of the second aspect, and vice versa.

Each and every embodiment, aspect and feature disclosed in the application from which priority is claimed is hereby optionally disclaimed.

BRIEF DESCRIPTION OF THE DRAWINGS

Embodiments of the invention will now be described, with reference to the accompanying drawings, in which.

DETAILED DESCRIPTION OF THE INVENTION

Figure 1:
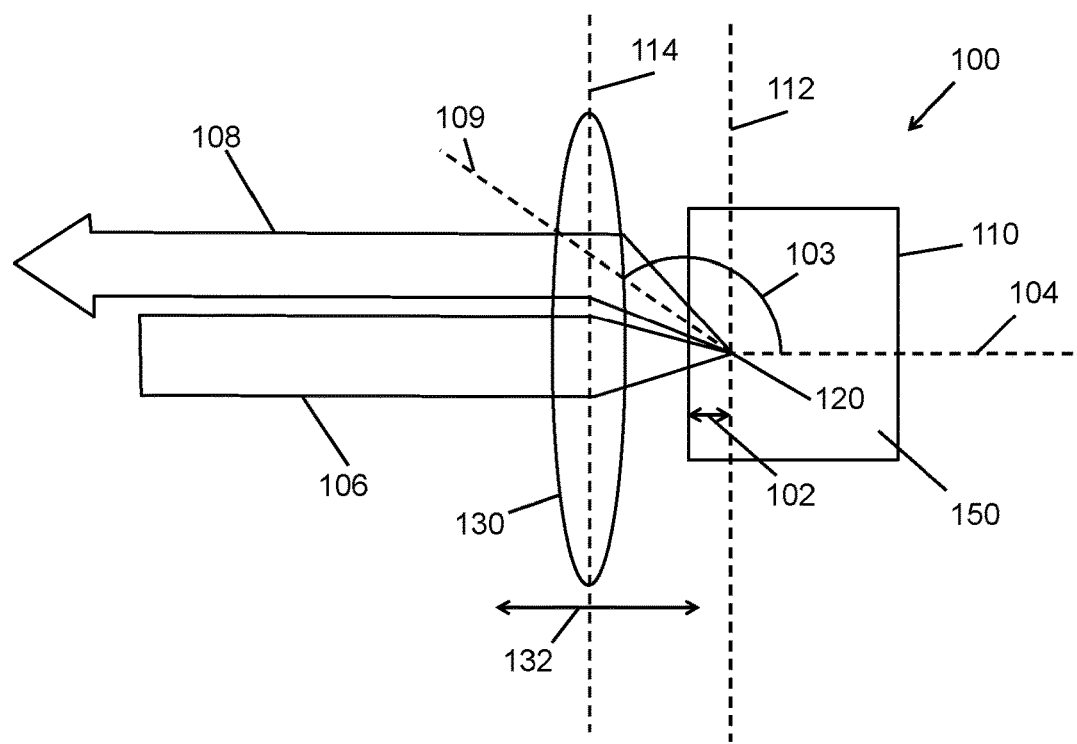
FIG. 1 is a schematic diagram of a prior art NIBS arrangement with the detection region in a first position.
Figure 2:
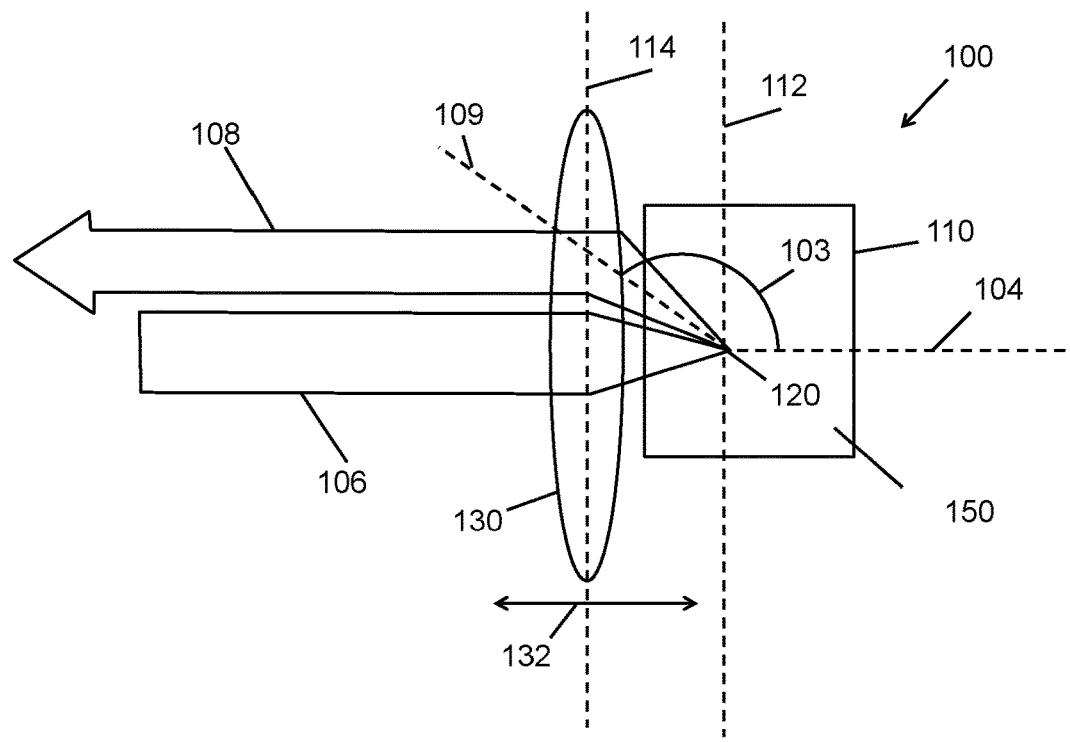
FIG. 2 is a schematic diagram of a prior art NIBS arrangement with the detection region in a second position.

Referring to FIGS. 1 and 2, a prior art NIBS arrangement 100 is shown, in which an illumination beam 106 is focussed on a sample 150 within a sample cell 110 by a focussing lens 130.

A detection optical path 108 receives light scattered from the illumination beam 106 by particles dispersed within the sample 150. The detection optical path 108 defines the field of view of a detector (not shown) for detecting the scattered light. The detection optical path 108 may receive light scattered at a narrow range of angles, centred on a specific scattering angle 103 along detection axis 109. The detection optical path 108 is also focussed within the sample 150 by the focussing lens 130.

The intersection of the illumination beam 106 and the detection optical path 108 define a detection region 120. The position of the detection region 120 within the sample cell 110 can be varied by moving the focussing lens 130, which varies the position of a focal plane 112 of the focussing lens 130 within the sample cell 110. As the focussing lens moves closer to the sample cell, the detection volume moves in the same direction, increasing a distance 102 between the detection region 120 and a cell wall through which the light beam 106 passes to illuminate the sample 150. In FIG. 1 the detection volume 120 is positioned closer to this wall of the sample cell 110 than is the case in FIG. 2.

As discussed above, this arrangement provides for adjustment of the position of the detection region 120, but does not enable adjustment of the volume of the detection region 120.

Figure 3:
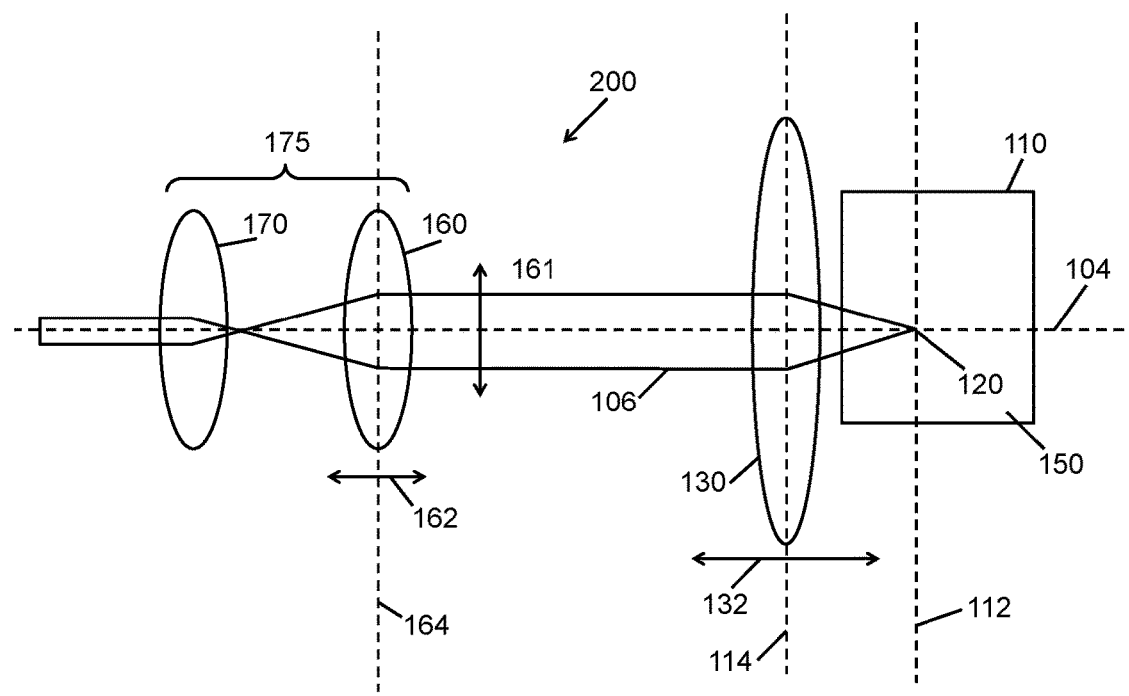
FIG. 3 is a schematic diagram of an illumination optical path in accordance with an embodiment in which a moveable lens is configured to vary the width of an illumination beam that is incident on the focussing lens.

Referring to FIG. 3, an illumination optical path 200 is shown comprising a beam expander 175, focussing lens 130 and sample cell 110. The beam expander 175 is arranged to receive an illuminating light beam 106 from a light source (not shown), and to vary the width 161 of the illuminating light beam 106 incident on the focussing lens 130. The illuminating light beam 106 defines a light beam axis 104.

The beam expander 175 in this embodiment comprises a fixed lens 170 and a moveable lens 160. The fixed lens 170 is disposed between the light source and the moveable lens 160, and is a converging lens. The moveable lens 160 is moveable along the light beam axis 104. The range of movement of the moveable lens 160 may occupy a position on the light beam axis that is after a focal plane of the fixed lens 170, so that the light beam 106 incident on the moveable lens 160 is diverging.

The moveable lens 160 may be configured to collimate the diverging light beam 106 following the focal plane of the fixed lens 170, so that the beam expander 175 produces a collimated beam of light 106 of variable beam width (or diameter) 161 incident on the focussing lens 130.

There is a Fourier relationship between the plane 114 of the focussing lens 130 and the plane 164 of the moveable lens 160, such that an increased beam diameter 161 incident on the focussing lens 130 results in a tighter waist of focus within the focal plane 112 within the sample 150. Conversely, a narrower beam diameter 161 incident on the focussing lens 130 results in a broader waist of focus within the focal plane 112 within the sample 150. A narrower waist of focus equates to a smaller detection region 120, and broader waist equates to a larger detection region 120.

Figure 5:
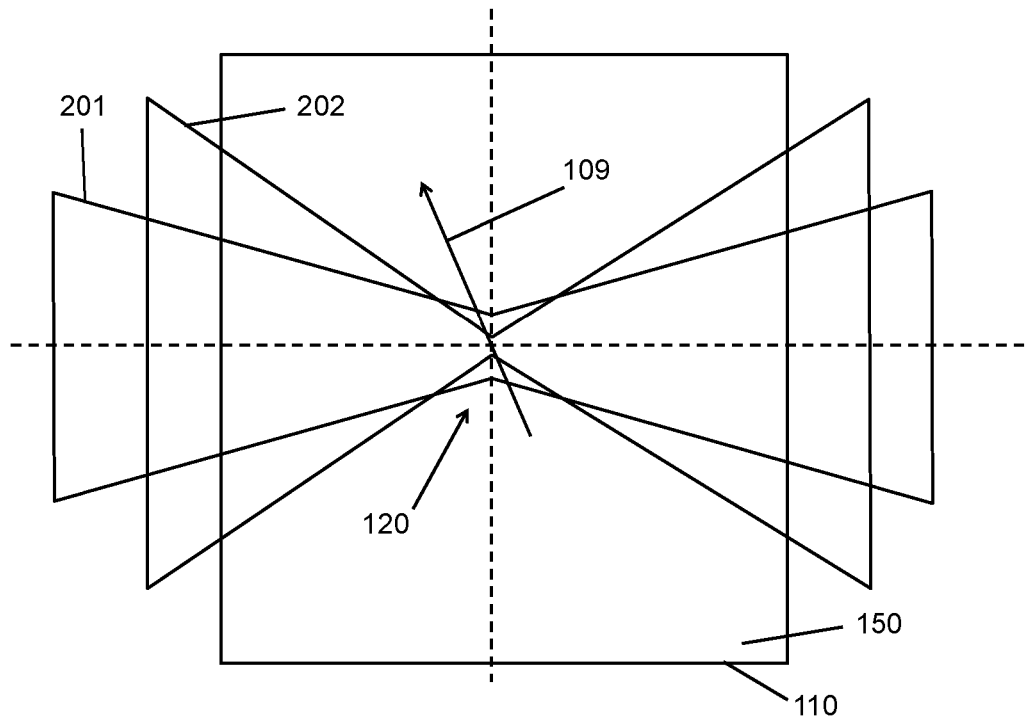
FIG. 5 is a schematic diagram of the detection region illustrating a beam waist for two different beam widths at the focusing lens.

FIG. 5 illustrates the relationship between the width of the beam at the focussing lens 130 and the size of the detection region 120. The path of a beam 201 that is narrow at the focussing lens 130 is compared with the path of a beam 202 that is broader at the focussing lens 130. It can be seen that the detection axis 109 intersects with a longer illuminated region of the sample for the bream 201 than for the beam 202. It will be appreciate that the detection optical path is not confined to the axis 109, but the relationship is nevertheless clear.

Moving the moveable lens 160 further from the fixed lens 170 results in a larger beam diameter 161, which provides a narrower beam waist at the focal plane 112 of the focussing lens 130, within the sample 150. Such a narrow beam waist is particularly suitable for characterization of turbid samples 150 with high concentration of particles. A detection region 120 with a smaller volume may be positioned closer to a wall of the sample cell 110, reducing the probability of multiple scattering, which directly results in an increase in the maximum particle concentration that can be reliably characterized by the instrument. For a sample with a low concentration of particles, the size of the detection region 120 may be increased by moving the moveable lens 160 further away from the fixed lens 170, thereby increasing the beam width at the focussing lens 130. The focussing lens 130 can be adjusted to place the detection region nearer to the centre of the sample cell 110, away from the walls, so as to minimise scattering contributions from the walls.

The arrangement depicted in FIG. 3 provides for independent adjustment of the location of the detection region within the sample cell 110 (e.g. nearer or further from the wall facing the light source) and the volume of the detection region 120.

The focussing lens 130 may operate in the same way as described with reference to FIGS. 1 and 2, being moveable so as to vary the position of the focal plane 112 within the sample cell 110, and therefore to vary the position of the detection region 120.

Although the detection optical path is not shown in FIG. 3, it may be similar to that depicted in FIGS. 1 and 2, with the detection optical path passing through the focussing lens 130, so that the focus of the detection optical path is likewise moved with the focusing lens 130.

In an alternative embodiment the converging fixed lens 170 may be replaced by a diverging fixed lens. Furthermore, the moveable focussing lens 130 may be replaced by a fixed, focus tuneable lens (e.g. a deformable lens and/or a lens with tuneable refractive index).

Figure 4:
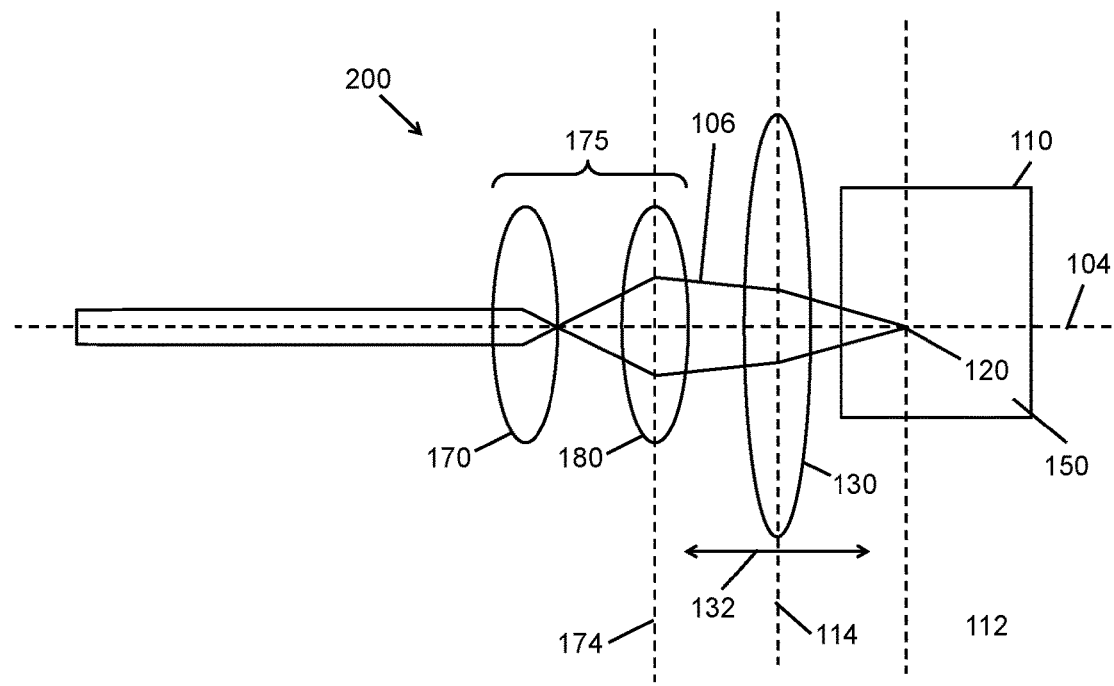
FIG. 4 is a schematic diagram of an illumination optical path in accordance with an embodiment in which a converging beam is incident on the moveable focussing lens.

Referring to FIG. 4, an alternative arrangement of an illumination optical path is shown, for use in an embodiment. The optical path comprises a beam expander 175, focussing lens 130 and sample cell 110. The focussing lens 130 and sample cell 110 may be as described with reference to FIG. 3.

The arrangement of FIG. 4 differs from that of FIG. 3 because in the arrangement of FIG. 4 the volume of the detection region 120 and the location of the detection region 120 are not independently adjustable. Instead, movement of the focussing lens 130 results in simultaneous adjustment of both the volume and location of the detection volume 120. This may be convenient, and provide a simpler arrangement with fewer moving parts.

The beam expander 175 in FIG. 4 comprises a first fixed lens 170 and a second fixed lens 180. The first fixed lens 170 is disposed between the second fixed lens 180 and the light source (not shown), and is a converging lens. The illuminating light beam 106 from the light source (which may be collimated) is incident on the first fixed lens 170. The second fixed lens 180 is positioned beyond the focal plane of the first fixed lens 170, between the first fixed lens 170 and the focussing lens 130, so the light beam 106 is diverging when it enters the second fixed lens 180. The second fixed lens 180 is arranged to produce a converging illumination beam at the moveable focussing lens 130. The width and taper of the illuminating beam 106 may be selected to provide a desired relationship between the position of the moveable focussing lens 130 (corresponding with a position of the detection region 120) and the volume of the detection region 120. In alternative arrangements, the first and second fixed lenses 170, 180 may be replaced by a single converging lens, or the first lens 170 could be a diverging lens.

Moving the focussing lens 130, closer to the beam expander 175 results in a broader beam incident on the focussing lens 130 resulting in a narrower beam waist within the sample 150 as the detection volume 120 is moved closer to the wall of the sample cell 110.

Figure 6:
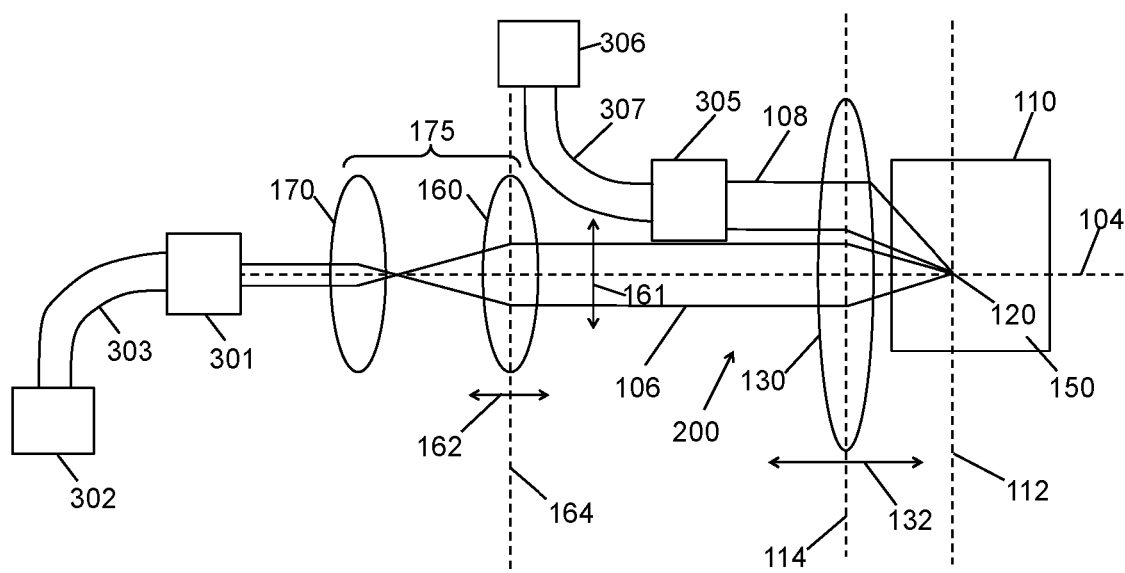
FIG. 6 is a schematic diagram of an embodiment of the invention, including the illumination optical path of FIG. 3.

Referring to FIG. 6, an example embodiment 300 is shown comprising the illumination arrangement 200 from FIG. 3. The detection optical path 108 is similar to that shown in FIGS. 1 and 2, and is focussed within the sample cell 110 by the focussing lens 130. The detection optical path 108 is coupled to a detection optical fibre 307 by a lens 305 (which may be a graded refractive index or GRIN lens). The detection optical fibre 307 couples the detection optical path 108 to the detector 306. Similarly, the light source 302 may provide illumination via an illumination optical fibre 303, via a fibre-free space coupling lens 301 (which may be a GRIN lens).

The detector 306 may provide a signal to a processor (not shown) which may perform a dynamic light scattering analysis to characterize particles within the sample 150. A display may be provided for displaying the results of such an analysis to a user.

The illumination path, i.e., the beam 106, and the detection path 108 may pass through a common lens, i.e. the focussing lens 130 in the arrangement illustrated in FIG. 6. In alternative arrangements, the detection path 108 may pass through a separate lens from the illumination path 106, for example in order to defocus one path with respect to the other.

Figure 7:
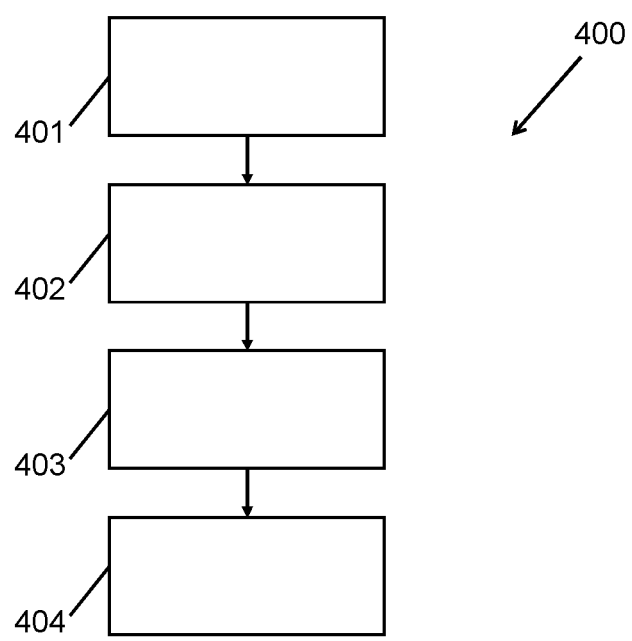
FIG. 7 is an outline flow diagram of a method of characterizing particles suspended in a sample, in accordance with an embodiment.

Referring to FIG. 7, an example method in accordance with an embodiment is shown. The method includes estimating or determining a concentration of particles within a sample 401. For instance, the concentration of particles within the fluid may be measured (e.g. by UV spectroscopy). Alternatively, the user may inspect the sample visually to determine a qualitative measure of particle concentration within the sample (e.g. to determine whether the sample appears turbid). A particle characterization instrument may be configured to automatically estimate the particle concentration, or a user may input an estimate of particle concentration.

Following the step 401 of estimating/determining particle concentration, the location and volume of the detection region is adjusted 402, for example in response to the concentration of particles in the sample.

Once the detection region is adjusted, the detection region is illuminated, and light scattered by interactions of the illuminating beam with the sample is detected 403 (e.g. at a detector). The illumination may take place along an optical path similar to those described above. Similarly, the detection may take place along an optical path like those described above.

The data obtained by detecting the scattered light is subsequently analysed 404 in accordance with well-known dynamic light scattering techniques, so as to determine characteristics of the particles of the sample from the detected scattered light. Such analysis may be performed using a processor, and the results may be displayed on a screen or recorded on a medium (e.g. a computer readable medium).

Although example embodiments have been depicted in which the detection optical path is configured to detect backscattered light, in other embodiments the detection optical path may be configured to detect forward scattered light (e.g. scattered at less than 90 degrees from the illumination light beam axis 104). Furthermore, an example has been described that uses an optical fibre to couple the detector and/or light source to the sample, it will be understood that the present invention is equally applicable to arrangements that use free space optics.

In the example embodiments a beam expander has been used to implement a variable volume detection region within the sample. However, any suitable optical assembly, optical component or components may be used to achieve this functionality. For example, a programmable or variable focal length lens may be used (e.g. having a variable refractive index or variable geometry). Alternatively, a plurality of detection paths may be used, each corresponding with a different detection volume, thereby avoiding the need to vary the width of the illuminating beam.

Embodiments have been described in which varying a beam width at the focussing lens is used to vary the detection region volume. In other embodiments, a focus tuneable lens may be used as the focussing lens, and the detection region volume may be varied by adjusting the focal length of the focus tuneable lens. The focus tuneable lens may be moveable, such that the location of the detection region can be adjusted independently of the detection region volume.

In some embodiments, both a variable beam width at the focussing lens and a focus tuneable focussing lens may be used.

Other variations and modifications will be apparent to the skilled person, and are intended to be within the scope of the invention, which is defined by the appended claims.

The invention claimed is:

1. A particle characterization apparatus comprising:
a sample cell for holding a sample;
a light source for producing a light beam for illuminating the sample in the sample cell, thereby producing scattered light by the interaction of the light beam with the sample;
a focussing lens for focussing the light beam within the sample; and
a detector for detecting the scattered light along a detection optical path that intersects the focussed light beam within the sample, the intersection of the focussed light beam and the detection optical path in the sample defining a detection region, wherein the apparatus comprises an optical arrangement for varying the volume of the detection region and the focussing lens is moveable, so as to vary a location of a focal plane of the light beam and detection optical path in the sample with movement of the focussing lens so as to vary the position of the detection region within the sample;
wherein the apparatus is operable to perform a dynamic light scattering measurement using an output from the detector;
wherein the optical arrangement for varying the light beam width incident on the focussing lens comprises:
a converging lens between the focussing lens and light source causing the light beam to be convergent or collimated at the focussing lens, and a mount operable to move the focussing lens so as to vary the distance between the focussing lens and the converging lens.

2. The apparatus of claim 1, wherein the optical arrangement for varying the volume of the detection region is operable to vary the light beam width incident on the focussing lens.

3. The apparatus of claim 2, wherein the optical arrangement for varying the light beam width incident on the focussing lens comprises a beam expander.

4. The apparatus of claim 3, wherein the beam expander comprises a moveable lens, operable to vary the light beam width incident on the focussing lens with movement of the moveable lens.

5. The apparatus of claim 4, wherein the beam expander further comprises a fixed lens between the light source and the moveable lens.

6. The apparatus of claim 5, wherein the beam expander is operable to produce a collimated output beam of variable width.

7. The apparatus of claim 5, wherein the fixed lens comprises a diverging lens.

8. The apparatus of claim 5, wherein the fixed lens comprises a converging lens.

9. The apparatus of claim 4, wherein the moveable lens comprises a converging lens.

10. The apparatus of claim 1, wherein the focussing lens focuses the detection optical path within the sample.

11. The apparatus of claim 10, wherein the detection optical path comprises an optical fibre.

12. The apparatus of claim 11, wherein the optical fibre comprises a single mode fibre.

13. The apparatus of claim 11, further comprising a coupling lens arranged to couple the detection optical path to the optical fibre.

14. The apparatus of claim 13, wherein the coupling lens comprises a graded refractive index lens.

15. The apparatus of claim 1, wherein the converging lens is a fixed lens.

16. The apparatus of claim 1, wherein the focussing lens comprises a focus tuneable lens.

17. The apparatus of claim 1, wherein the apparatus comprises a processor for performing the dynamic light scattering measurement.

* * * * *